United States Patent [19]

Kawashima

[11] 4,292,961
[45] Oct. 6, 1981

[54] APPARATUS FOR AUTOMATICALLY CONTROLLING THE POSITION OF ENDOSCOPES OR SIMILAR DEVICES IN A CAVITY

[75] Inventor: Kazuma Kawashima, Tokyo, Japan

[73] Assignee: Olympus Optical Company Ltd., Tokyo, Japan

[21] Appl. No.: 93,160

[22] Filed: Nov. 13, 1979

[30] Foreign Application Priority Data

Dec. 26, 1978 [JP] Japan ............................. 53-162730

[51] Int. Cl.³ .............................................. A61B 1/06
[52] U.S. Cl. .................................... 128/6; 33/178 F
[58] Field of Search ................ 128/4, 6, DIG. 9, 772; 254/134.3 FT; 15/104.3 SN; 250/256, 265, 268, 358 P; 33/302, 178 E, 178 F

[56] References Cited

U.S. PATENT DOCUMENTS

| 3,744,906 | 7/1973 | Sato et al. | 128/6 X |
| 3,889,662 | 6/1975 | Mitsui | 128/6 |
| 4,054,128 | 10/1977 | Seufert et al. | 128/4 |
| 4,199,258 | 4/1980 | Dau | 33/125 B X |

FOREIGN PATENT DOCUMENTS

| 50-25083 | 3/1975 | Japan | 128/4 |
| 53-42481 | 4/1978 | Japan | 128/4 |

Primary Examiner—Michael H. Thaler
Attorney, Agent, or Firm—Weinstein & Sutton

[57] ABSTRACT

Apparatus for automatically controlling the position of a device in a cavity includes a light emitter and light sensors disposed in a distal end of the device for determining the position of the distal end within the cavity. When the device is inserted into the cavity, light is emitted from the emitter toward the internal wall of the cavity, and the reflected light is received by the sensors. The reflected light received by the sensors is utilized to automatically control the position of the device in the cavity.

23 Claims, 11 Drawing Figures

APPARATUS FOR AUTOMATICALLY CONTROLLING THE POSITION OF ENDOSCOPES OR SIMILAR DEVICES IN A CAVITY

BACKGROUND OF THE INVENTION

The invention relates to an apparatus for automatically controlling the positioning of a device, such as an endoscope, and more particularly, to such apparatus in which the degree and orientation of bending of a bendable portion of the device is autonomously controlled so that its distal end is always centrally located within a cavity in which the device is being inserted.

As is well known in the prior art, flexible endoscopes adapted for insertion into a body cavity for medical purposes include a bendable portion located adjacent to the distal end of the endoscope. The bending of the bendable portion is manually controlled from the proximal end of the endoscope. By bending the bendable portion, the distal end can be oriented in any desired direction.

When such a flexible endoscope is inserted into a body cavity, an eyepiece assembly disposed in the proximal end, which is located outside the body cavity, can be utilized to observe the interior of the cavity so that the distal end is centrally located therein as it is being inserted. However, the process of inserting the distal end so that it is centrally located within the cavity involves a composite procedure including the steps of twisting the entire portion of the endoscope which is inserted into the cavity, bending the bendable portion of the endoscope, and advancing or retracting the endoscope portion located within the cavity, all of which steps are selectively utilized in a suitable combination in accordance with the bends or the increased or reduced spaces of the cavity. Hence, the procedure is very difficult to perform, requiring a high level of skill. In particular, when inserting the endoscope into a cavity, such as the tortuous cavity of the large intestine, even a skilled operator requires an increased length of time to insert the endoscope, and may cause unintended pain to a patient. In addition, the location where the endoscope can be admitted may be disadvantageously limited.

SUMMARY OF THE INVENTION

In accordance with the invention, there is provided a new and improved apparatus for automatically controlling the positioning of a device, such as an endoscope, in a cavity. In accordance with the improvement, the apparatus is provided, in its distal portion, with a light emitting mechanism and a light sensing mechanism. The light sensing mechanism receives light emitted from the light emitting mechanism and reflected from an internal wall of a cavity in which the distal portion is being inserted. A control mechanism, which is responsive to the amount of light received by the light sensing mechanism, automatically controls the position of the distal portion in the cavity in which the distal portion is being inserted.

In one embodiment, the light sensing mechanism includes a plurality of light sensors, each of which is adapted to generate signals responsive to the amount of sensed light. Inasmuch as the respective signals generated by the light sensors are dependent on the distance between the distal portion, which is bendable, and the internal wall of the cavity in an inversely proportional manner, these signals can be utilized to automatically control the bending of the bendable distal portion so as to centrally locate the distal portion within a cavity, thereby permitting a smooth insertion of the device.

The distal portion of the device can be autonomously controlled, so that no particular skill is required for the insertion of the device into a tortuous cavity, such as the large intestine, whereby the insertion procedure can be completed within a reduced period of time and in a smooth and painless manner. By reducing the insertion time, the device becomes available for more frequent use.

DESCRIPTION OF PREFERRED EMBODIMENTS

While the present invention is applicable to any type of device adapted to perform a particular operation in a cavity, it is especially suitable for use with an endoscope. Thus, the invention will be described with particular reference to an endoscope.

Figure 1:
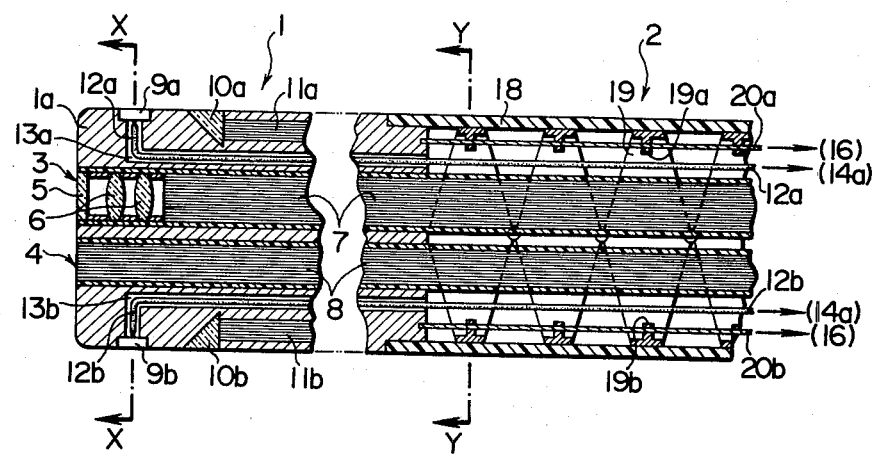
FIG. 1 is an enlarged longitudinal section of an apparatus for automatic bending control of an endoscope according to one embodiment of the invention.

FIG. 1 is an enlarged longitudinal section of an endoscope and, in particular, a distal end and a bendable portion thereof. The endoscope includes apparatus for automatically controlling the orientation and degree of bending of the bendable portion. Specifically, the endoscope includes distal end 1 which represents a foremost region of the portion thereof adapted to be inserted into a cavity. The distal end 1 is formed by cylindrical member 1a and constructed in quite the same manner as one for conventional endoscope except that ranging light emitters 10a to 10d (10c, 10d being not shown) and ranging light sensors 9a to 9d (see FIG. 2) which form part of the bending control apparatus of the invention are disposed therein. Thus, cylindrical member 1a has a front end face which has a centrally positioned observation window 3 and illumination window 4 directly below the observation window 3 and in vertical alignment therewith. Cover glass 5 is fitted into observation window 3 in a water tight manner, and objective lens system 6 is disposed inside the window 3 adjacent to the cover glass 5. An image guide formed by a bundle of optical fibres 7 has its front end face disposed adjacent to the objective lens system 6 so that light passing through the objective lens system 6 impinges on the optical fibres 7. A light guide formed by a bundle of optical fibres 8 is fitted into and secured in illumination window 4 in a water tight manner so as to expose the outer end faces of the fibres 8 for emitting light therefrom.

Ranging light emitters 10a to 10d each comprise a reflecting prism having a light emitting surface which is coextensive with the outer peripheral surface of cylindrical member 1a. The ranging light emitters 10a to 10d are disposed at an angular interval of 90° in the peripheral surface of distal end 1 in a water tight manner. Each of ranging light emitters 10a to 10d also includes a light incident surface which is in abutment against the light emitting, end face of a corresponding one of optical fibre bundles 11a to 11d (11c, 11d being not shown) which form ranging light guides. These optical fibre bundles 11a to 11d function in the same manner as optical fibres 8 to lead ranging light from a light source assembly, which is disposed within the operating end of the endoscope, to the light emitting end faces thereof. An equal amount of light is emitted from each of emitters 10a to 10d. The light emitted from the ranging light emitters 10a to 10d is directed in a radial direction with respect to the distal end 1.

Ranging light sensors 9a to 9d are formed by light receiving elements, which are adapted to produce an electromotive force in response to reflected light from the inner wall of the cavity which is irradiated by light from the emitters 10a to 10d. These sensors 9a to 9d are disposed in the external surface of cylindrical member 1a in a water tight manner toward its front end at an angular interval of 90° (see FIG. 2) so that their light receiving or incident surfaces are coextensive with the external surface of distal end 1. It is to be understood that each of the sensors 9a to 9d is aligned with a corresponding one of the emitters 10a to 10d, respectively, in such a manner that the sensor and emitter of each sensor-emitter set lie in a plane substantially parallel to a longitudinal axis of the the axial direction of distal end 1. In this manner, emitters 10a to 10d and the sensors 9a to 9d form four sensor-emitter sets which are spaced apart 90° around the external surface of distal end 1. Cylindrical member 1a is formed with circumferentially spaced, radially extending guide holes 13a to 13d (see FIG. 2) through which lead wires 12a to 12d, respectively, extend to conduct the outputs from the sensors 9a to 9d, respectively, to a bending control mechanism which is located within the operating or proximal end of the endoscope.

Figure 4:
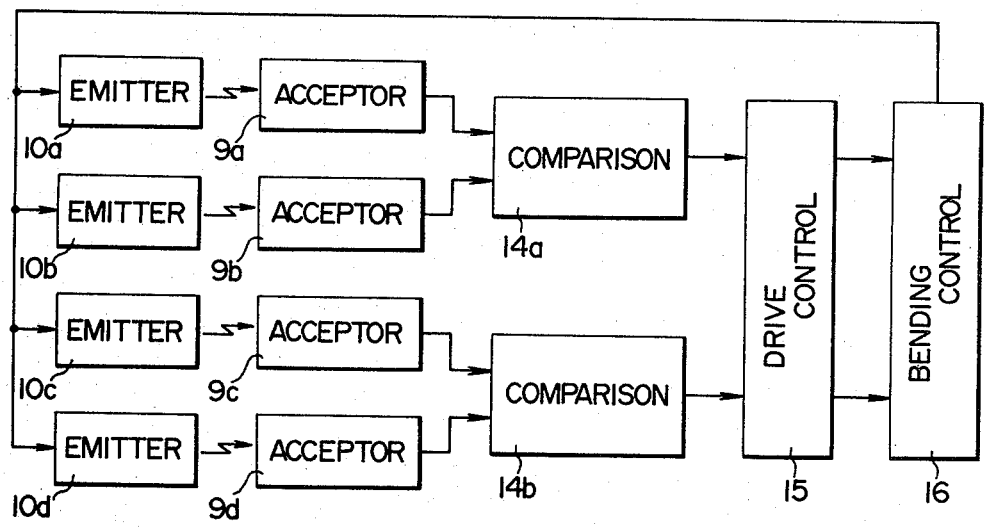
FIG. 4 is a block diagram illustrating the arrangement of a bending control mechanism associated with the apparatus shown in FIG. 1.

The bending control mechanism is shown in FIG. 4, and comprises comparison circuit 14a for receiving the outputs from the sensors 9a, 9b which are disposed on the top and bottom positions on the peripheral surface of the distal end 1 for determining a vertical position of distal end 1 within the cavity. A comparison circuit 14b receives the outputs from the sensors 9c and 9d which are disposed on the left-hand and right-hand side of the peripheral surface of the distal end 1 for determining a lateral position of distal end 1 within the cavity. A drive control circuit 15, which is responsive to the outputs from the pair of comparison circuits 14a, 14b, produces a control signal. A bending drive mechanism 16, including conventional traction means, is responsive to the control signal from drive control circuit 15.

As shown in FIG. 1, a bendable portion 2, which continues to the distal end 1, includes flexible outer sleeve 18 which has its front end fixedly connected to the rear end of cylindrical member 1a. The sleeve 18 houses a plurality of conventional ring-shaped bending fixtures 19, which are adapted for articulation with respect to each other. The foremost one of the fixtures 19 has its front end mounted on the rear end of cylindrical member 1a to serve as a support which prevents bendable portion 2 from being collapsed while permitting its bending operation. Each of the fixtures 19 internally carries guides 19a to 19d (see FIG. 3) which are circumferentially spaced apart and through which operating wires 20a to 20d, respectively, extend. Each of the wires 20a to 20d is secured, at one end, to the rear end of cylindrical member 1a and, at the other end, to the bending drive mechanism 16 disposed within the operating end of the endoscope. In this manner, the bending drive mechanism 16 can be operated to pull or release operating wires 20a to 20d to permit the bendable portion 2 to be bent or returned to its unbent position. Specifically, if upper and lower wires 20a, 20b are either pulled or released, the bendable portion 2 can be bent in the vertical direction or returned to its unbent position. Similarly, if left-hand and right-hand wires 20c, 20d are either pulled or released, the bendable portion 2 can be bent in the lateral direction or returned to its unbent position.

Figure 5:
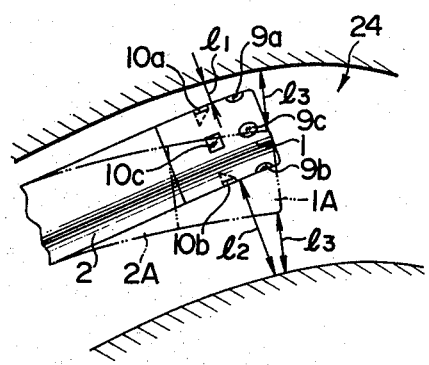
FIGS. 5 and 6 are a plan view and a front view of the apparatus shown in FIG. 1, illustrating its operations.
Figure 6:
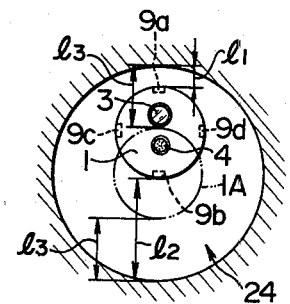

The operation of the apparatus will now be described with reference to FIGS. 5 and 6 which show a longitudinal and a transverse section of hollow cavity 24. If the distal end 1 is displaced toward the upper wall of the cavity 24, light emitted from emitter 10a will be reflected by the upper internal surface of the cavity 24 to impinge on light sensor 9a after travelling through a distance which corresponds to twice the distance $l_1$ between the emitter 10a and the wall. Similarly, light emitted by emitter 10b will be reflected by the lower internal wall surface of the cavity 24 to impinge on the sensor 9b after travelling through a distance which substantially corresponds to twice the distance $l_2$ between emitter 10b and the lower wall surface.

Both emitters 10a and 10b are designed to emit an equal amount of ranging light therefrom, so that the amount of light received by respective sensors 9a, 9b will be inversely proportional to the distances $l_1$ and $l_2$. Since voltages $V_1$, $V_2$ developed by the sensors 9a, 9b, respectively, are proportional in magnitude to the amount of light received by them, it will be seen that in the present example where the distal end 1 is displaced toward the upper wall of the cavity 24, or when $l_1 < l_2$, $V_1 > V_2$. These voltages $V_1$, $V_2$ are supplied to comparison circuit 14a shown in FIG. 2, which compares the magnitude of these voltages, and upon detecting the inequality $V_1 > V_2$, determines that the distal end 1 is displaced toward the upper wall of the cavity 24. A corresponding decision signal is applied to drive control circuit 15, which responds thereto by producing a control signal to release operating wire 20a and to pull operating wire 20b. In response to this control signal, bending drive mechanism 16 releases wire 20a and pulls wire 20b, whereby bendable portion 2 is bent toward the lower internal wall of the cavity 24, thus autonomously shifting the distal end 1 and bendable portion 2 to a central position within the cavity 24, as represented by phantom lines 1A and 2A. At this central position, the distance between the sensor 9a and the upper wall of the cavity 24 and the distance between the lower wall and the sensor 9b will have an equal value $l_3$. Hence, the amount of light received by respective sensors 9a, 9b will become substantially equal to each other, whereby the voltages $V_1$, $V_2$ will have substantially equal magnitudes. Hence, comparison circuit 14a detects the equality $V_1 = V_2$, and determines that the distal end 1 is centrally located within the cavity 24. A corresponding signal is applied to drive control circuit 15, which responds thereto by terminating the control signal mentioned above. Consequently, the bendable portion 2 ceases to be bent further downward, and the distal end 1 can be inserted deeper into the cavity 24 while being maintained in the center thereof.

It will be appreciated that when the distal end 1 is displaced toward the lower wall of the cavity 24, the opposite process takes place, i.e., the operating wire 20a is pulled and the operating wire 20b is released to permit the bendable portion 2 to be bent toward the upper wall of the cavity 24 until the distal end 1 is autonomously located at the center of the cavity 24.

Furthermore, if the distal end 1 is laterally displaced toward either left-hand or right-hand sidewall within cavity 24, a similar procedure occurs. Specifically, light emitted by emitters 10c, 10d impinges on corresponding sensors 9c, 9d, whereby operating wires 20c, 20d are either pulled or released until distal end 1 is autonomously shifted to the center of the cavity 24.

In this manner, the bendable portion 2 is autonomously controlled if the distal end 1 of the endoscope assumes an offset position within the cavity 24, allowing the distal end 1 to be maintained centrally within the cavity 24. Hence, it is only necessary for the operator to insert the endoscope into the cavity without causing any abutment of the distal end 1 against the internal wall surface of the cavity 24. No particular skill is required for the insertion, which can be completed within a reduced length of time since the manual operation of bending the bendable portion 2 or twisting the entire endoscope at the operating end is no longer required.

Figure 2:
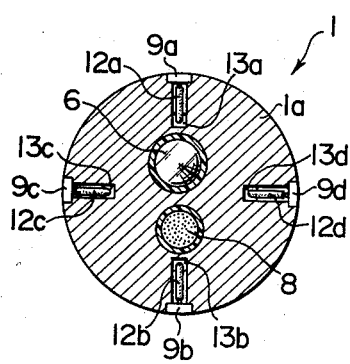
FIGS. 2 and 3 are cross sections taken along the lines X—X and Y—Y shown in FIG. 1.
Figure 3:
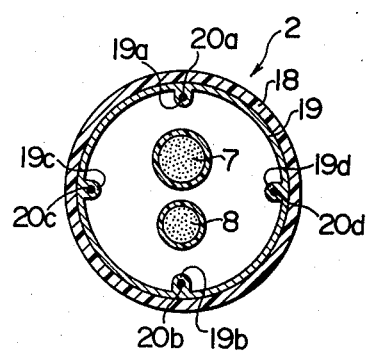
Figure 7:
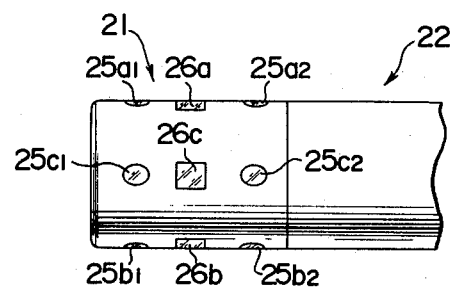
FIG. 7 is an enlarged fragmentary plan view of an apparatus for automatic bending control of an endoscope according to another embodiment of the invention.

FIG. 7 shows another embodiment of the invention which represents an improvement over the apparatus shown in FIGS. 1 to 3. In the apparatus of FIGS. 1 to 3, the sensors 9a to 9d are located adjacent to their corresponding emitters 10a to 10d. However, in the embodiment of FIG. 7, each of light emitters 26a to 26d, which are circumferentially spaced apart at an equal angular interval around the peripheral surface of distal end 21, is associated with a pair of light sensors 25a1, 25a2; 25b1, 25b2; 25c1, 25c2; or 25d1, 25d2 (25d1, 25d2 being not shown).

Figure 8:
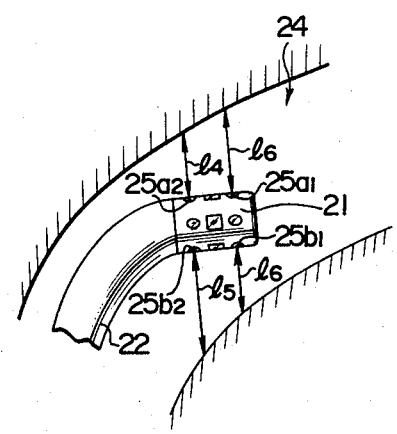
FIGS. 8 and 9 are plan views illustrating the use of the apparatus shown in FIG. 7.
Figure 9:
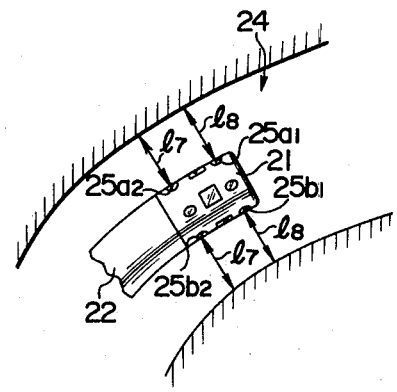

With this apparatus, it will be understood from FIG. 8 that when distal end 21 assumes a position such that the distance from the sensor 25a1, which is located nearest to the front end of distal end 21, to the internal wall surface of cavity 24 has a value which is equal to the distance from sensor 25b1 to the internal wall surface, the orientation of the distal end 21 may nevertheless not coincide with that of the cavity 24 because distance l$_4$ from sensor 25a2, located remote from the front end of distal end 21, to the internal wall surface of cavity 24 is different from distance l$_5$ from the sensor 25b2 to the internal wall surface. By bending a bendable portion 22 of the distal end 21, the distal end 21 can be properly aligned with the cavity 24 as shown in FIG. 9, with the distances from the sensors 25a1 and 25b1 to the inner wall surface of the cavity 24 having an equal distance l$_8$ and the distances from the sensors 25a2 and 25b2 to the internal wall surface of the cavity 24 having an equal distance l$_7$. In this manner, a smooth insertion of the distal end 21 into the cavity 24 is assured.

Figure 10:
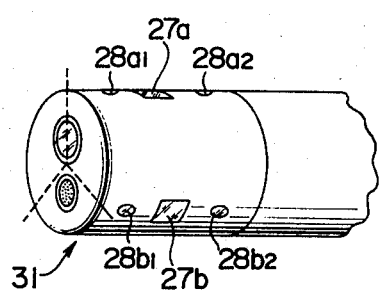
FIGS. 10 and 11 are enlarged perspective views of apparatus for automatic bending control of an endoscope according to further embodiments of the invention.

FIG. 10 shows a further embodiment of the invention which is a slight modification of the apparatus shown in FIG. 7 in that three light emitters 27a to 27c and three pairs of light sensors 28a1, 28a2; 28b1, 28b2; 28c1, 28c2 are circumferentially disposed around the peripheral surface of distal end 31 at an equal angular interval, in contradistinction to four light emitters 26a to 26d and four pairs of acceptors 25a1 to 25d2 shown in FIG. 7. It will be appreciated that a similar effect and operation can be to the manner of operation of the embodiment of FIG. 7.

Figure 11:
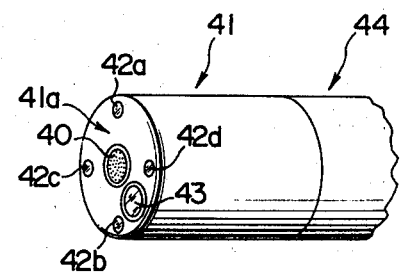

FIG. 11 shows still another embodiment of the invention in which illumination light, emitted through an illumination window 40 located in a front end face 41a of a distal end 41 of an endoscope, is utilized as ranging light. In this embodiment illumination window 40 is centrally disposed in front end face 41a of distal end 41 and surrounded by four light sensors 42a to 42d which are circumferentially spaced apart at equal angular intervals. This design simplifies the arrangement for the automatic bending control apparatus. Although this embodiment emits ranging light in a direction which is different from the direction in which ranging light is emitted in the embodiment illustrated in FIGS. 1 to 3, bendable portion 44 of the distal end 41 is autonomously controlled such that there is no opposing cavity wall in front of the front end face 41a of the distal end 41, thus achieving an effect similar to the effect achieved by the embodiment shown in FIGS. 1 to 3. In FIG. 11, an observation window 43 is also disposed in the front end face 41a of the distal end 41.

What is claimed is:

1. Apparatus for controlling the position of a device adapted for insertion in a cavity, comprising a bendable distal portion on said device, light emitter means located on said distal portion of the device for directing light toward an internal wall of a cavity in which said distal portion is being inserted, light sensing means located on said distal portion for sensing light emitted from said light emitting means and reflected from an internal wall of a cavity in which said distal portion is being inserted and for producing signals in response to the amount of sensed light, control means located at the proximal portion of said device and responsive to the amount of reflected light sensed by said light sensing means, said control means including comparison means for comparing signals produced by said light sensing means to determine the position of said distal portion in a cavity in which said distal portion is being inserted, and drive means responsive to the position determination made by said comparison means for automatically controlling the position of said distal portion in a cavity in which said distal portion is being inserted.

2. Apparatus according to claim 1, wherein said light sensing means includes a plurality of spaced-apart light sensors.

3. Apparatus according to claim 2, wherein said light emitting means is located on a free end of said distal portion.

4. Apparatus according to claim 3, wherein said light sensors are located on said free end of said distal portion about said light emitting means.

5. Apparatus according to claim 4, wherein said light emitting means is a single light emitter.

6. An apparatus according to claim 5, wherein said free end of said distal portion has a generally circular shape and said plurality of light sensors includes a first pair of light sensors positioned diametrically opposite each other and a second pair of light sensors positioned diametrically opposite each other, one light sensor of said first pair of light sensors being spaced a first distance from one light sensor of said second pair of light sensors and a second distance, equal to said first distance, from the other light sensor of said second pair of light sensors, the other light sensor of said first pair of light sensors being spaced a third distance, equal to said second distance, from said one light sensor of said second pair of light sensors and a fourth distance, equal to said third distance, from said other light sensor of said first pair of light sensors, said one light sensor of said second pair of light sensors being spaced a fifth distance, equal to said fourth distance, from said one light sensor of said first pair of light sensors and a sixth distance, equal to said fifth distance, from said other light sensor of said first pair of light sensors, said other light sensor of said second pair of light sensors being spaced a seventh distance, equal to said sixth distance, from said one light sensor of said first pair of light sensors and an eighth distance, equal to said seventh distance, from said other light sensor of said first pair of light sensors.

7. Apparatus according to claim 6, wherein each of said light sensors of said first and second pairs of light sensors is spaced substantially adjacent to a circumferential edge of said free end of said distal portion.

8. Apparatus according to claim 7, wherein said device is an endoscope having illumination means for observing an interior of a cavity in which said endoscope is being inserted, said illumination means forming said light emitter.

9. Apparatus according to claim 2, wherein said light emitting means includes a plurality of light emitters, each of said light emitters being located on a peripheral surface of said distal portion.

10. Apparatus according to claim 9, wherein each of said light sensors is located on a peripheral surface of said distal portion.

11. Apparatus according to claim 10, wherein said distal portion has a generally cylindrical shape and said plurality of light emitters includes a first pair of light emitters positioned diametrically opposite each other and a second pair of light emitters positioned diametrically opposite each other, one light emitter of said first pair of light emitters being spaced a first distance from one light emitter of said second pair of light emitters and a second distance, equal to said first distance, from the other light emitter of said second pair of light emitters, the other light emitter of said first pair of light emitters being spaced a third distance, equal to said second distance, from said one light emitter of said second pair of light emitters and a fourth distance, equal to said third distance, from said other light emitter of said first pair of light emitters, said one light emitter of said second pair of light emitters being spaced a fifth distance, equal to said fourth distance, from said one light emitter of said first pair of light emitters and a sixth distance, equal to said fifth distance, from said other light emitter of said first pair of light emitters, said other light emitter of said second pair of light emitters being spaced a seventh distance, equal to said sixth distance, from said one light emitter of said first pair of light emitters and an eighth distance, equal to said seventh distance, from said other light emitter of said first pair of light emitters.

12. Apparatus according to claim 4, wherein said plurality of light sensors includes a first pair of light sensors, one light sensor of said first pair of light sensors being positioned adjacent to said one light emitter of said first pair of light emitters and the other light sensor of said first pair of light sensors being positioned adjacent to said other light emitter of said first pair of light emitters, and a second pair of light sensors, one light sensor of said second pair of light sensors being positioned adjacent to said one light emitter of said second pair of light emitters and the other light sensor of said second pair of light sensors being positioned adjacent to said other light emitter of said second pair of light emitters.

13. Apparatus according to claim 12, wherein said plurality of light sensors further includes a third pair of light sensors, one light sensor of said third pair of light sensors being positioned adjacent to said one light emitter of said first pair of light emitters and the other light sensor of said third pair of light sensors being positioned adjacent to said other light emitter of said first pair of light emitters, and a fourth pair of light sensors, one light sensor of said fourth pair of light sensors being positioned adjacent to said one light emitter of said second pair of light emitters and the other light sensor of said fourth pair of light sensors being positioned adjacent to said other light emitter of said second pair of light emitters.

14. Apparatus according to claim 13, wherein said one light sensor of said first pair of light sensors is positioned to a first side of said one light emitter of said first pair of light emitters; said one light sensor of said third pair of light sensors is positioned to a second side of said one light emitter of said first pair of light emitters, said second side of said one light emitter of said first pair of light emitters being opposite said first side of said one light emitter of said first pair of light emitters; said other light sensor of said first pair of light sensors is positioned to a first side of said other light emitter of said first pair of light emitters; said other light sensor of said third pair of light sensors is positioned to a second side of said other light emitter of said first pair of said light emitters, said second side of said other light emitter of said first pair of light emitters being opposite said first side of said other light emitter of said first pair of light emitters; said one light sensor of said second pair of light sensors is positioned to a first side of said one light emitter of said second pair of light emitters; said one light sensor of said fourth pair of light sensors is positioned to a second side of said one light emitter of said second pair of light emitters, said second side of said one light emitter of said second pair of light emitters being opposite said first side of said one light emitter of said second pair of light emitters; said other light sensor of said first pair of said light sensors is positioned to a first side of said other light emitter of said first pair of light emitters; said other light sensor of said third pair of light sensors is positioned to a second side of said other light emitter of said first pair of light emitters, said second side of said other light emitter of said first pair of light emitters being opposite said first side of said other light emitter of said first pair of light emitters; said other light sensor of said second pair of light sensors is positioned to a first side of said other light emitter of said second pair of light emitters; and said other light sensor of said fourth pair of light sensors is positioned to a second side of said other light emitter of said pair of light emitters, said second side of said other light emitter of said second pair of light emitters being opposite said first side of said other light emitter of said second pair of light emitters.

15. Apparatus according to claim 14, wherein said one light emitter of said first pair of light emitters, said one light sensor of said first pair of light sensors and said one light sensor of said third pair of light sensors lie in a plane substantially parallel to a longitudinal axis of said distal portion; said other light emitter of said first pair of light emitters, said other light sensor of said first pair of light sensors and said other light sensor of said third pair of light sensors lie in a plane substantially parallel to a longitudinal axis of said distal portion; said one light emitter of said second pair of light emitters, said one light sensor of said second pair of light sensors and said one light sensor of said fourth pair of light sensors lie in a plane substantially parallel to a longitudinal axis of said distal portion; and said other light emitter of said second pair of light emitters, said other light sensor of said second pair of light sensors and said other light sensor of said fourth pair of light sensors lie in a plane substantially parallel to a longitudinal axis of said distal portion.

16. Apparatus according to claim 10, wherein said distal portion has a generally cylindrical shape and said light emitters include a first light emitter, and second light emitter spaced a first distance from said first light emitter, and a third light emitter spaced a second distance, equal to said first distance, from said first light emitter and a third distance, equal to said second distance, from said second light emitter, said first, second and third light emitters lying in a plane substantially perpendicular to a longitudinal axis of said distal portion.

17. Apparatus according to claim 16, wherein said plurality of light sensors includes a first light sensor positioned adjacent to said first light emitter, a second light sensor positioned adjacent to said second light emitter and a third light sensor positioned adjacent to said third light emitter.

18. Apparatus according to claim 17, wherein said plurality of light sensors further includes a fourth light sensor positioned adjacent to said first light emitter, a fifth light sensor positioned adjacent to said second light emitter and a sixth light sensor positioned adjacent to said third light emitter.

19. Apparatus according to claim 18, wherein said first light sensor is positioned to a first side of said first light emitter; said fourth light sensor is positioned to second side of said first light emitter, said second side of said first light emitter being opposite said first side of said first light emitter; said second light sensor is positioned to a first side of said second light emitter; said fifth light sensor is positioned to a second side of said second light emitter, said second side of said second light emitter being opposite said first side of said second light emitter; said third light sensor is positioned to a first side of said third light emitter; and said sixth light sensor is positioned to a second side of said third light emitter, said second side of said third light emitter being opposite said first side of said third light emitter.

20. Apparatus according to claim 19, wherein said first light emitter, said first light sensor and said fourth light sensor lie in a plane substantially parallel to a longitudinal axis of said distal portion; said second light emitter, said second light sensor and said fifth light sensor lie in a plane substantially parallel to a longitudinal axis of said distal portion; and said third light emitter, said third light sensor and said sixth light sensor lie in a plane substantially parallel to a longitudinal axis of said distal portion.

21. Apparatus according to claim 1, further comprising bending means for bending said distal portion.

22. Apparatus according to claim 22, wherein each of said light sensors includes generating means for generating said signals in response to the amount of sensed light.

23. Apparatus according to claim 1, wherein said comparison means and said drive means cooperate to centrally locate said distal portion in a cavity in which said distal portion is being inserted.

* * * * *

UNITED STATES PATENT AND TRADEMARK OFFICE
CERTIFICATE OF CORRECTION

PATENT NO. : 4,292,961
DATED : October 6, 1981
INVENTOR(S) : Kazuma Kawashima

It is certified that error appears in the above—identified patent and that said Letters Patent is hereby corrected as shown below:

Claim 12, column 7, line 62, change "Claim 4" to --Claim 11--.

Claim 22, column 10, line 30, change "Claim 22" to --Claim 21--.

Signed and Sealed this

Eighth Day of June 1982

|SEAL|

Attest:

Attesting Officer

GERALD J. MOSSINGHOFF
Commissioner of Patents and Trademarks